United States Patent [19]

Peet et al.

[11] Patent Number: 5,099,037
[45] Date of Patent: Mar. 24, 1992

[54] 2,19-METHYLENEOXY AND 2,19-METHYLENETHIO BRIDGED STEROIDS AS AROMATASE AND 19-HYDROXYLASE INHIBITORS

[75] Inventors: Norton P. Peet, Cincinnati; J. O'Neal Johnston, Milford; Joseph P. Burkhart, West Chester, all of Ohio

[73] Assignee: Merrell Dow Pharmaceuticals Inc., Cincinnati, Ohio

[21] Appl. No.: 674,640

[22] Filed: Mar. 25, 1991

Related U.S. Application Data

[63] Continuation-in-part of Ser. No. 453,441, Dec. 20, 1989, abandoned.

[51] Int. Cl.⁵ .................. C07D 311/78; C07D 335/04
[52] U.S. Cl. ........................................ 549/382; 549/24
[58] Field of Search ................... 549/382, 24

[56] References Cited

U.S. PATENT DOCUMENTS 3,166,553  1/1965  Counsell et al. .
3,627,756  12/1971  Klimstra .
3,954,980  5/1976  Barton et al. .
4,814,324  3/1989  Borris et al. .

OTHER PUBLICATIONS

Caspi et al., *Chem. Abs.*, 65, 763g (1966).
Wicha et al., *Tetrahedron*, 25, 3961 (1969).
Luthy et al., *Helv. Chim. Acta*, 58, 1120 (1975).
Kocovsky, *J. Org. Chem.*, 53, 5816 (1988).
Armas et al., *J. Chem. Soc. Perkin Trans. I*, 1989, 405.
Njar et al., *Heterocycles*, 28, 1051 (1989).

*Primary Examiner*—Nicky Chan
*Attorney, Agent, or Firm*—John J. Kolano

[57] ABSTRACT

The present invention is directed to a group of compounds which are 2,19-methylenoxy or 2,19-methylenethio bridged steroids, and related steroidal compounds. These compounds are useful as aromatase and 19-hydroxylase inhibitors.

6 Claims, No Drawings

2,19-METHYLENEOXY AND 2,19-METHYLENETHIO BRIDGED STEROIDS AS AROMATASE AND 19-HYDROXYLASE INHIBITORS

The present application is a continuation-in-part of application Ser. No. 07/453,441, filed Dec. 20, 1989, and now abandoned.

BACKGROUND OF THE INVENTION

The estrogen hormones, estrone and estradiol, are involved in many physiological processes. The formation of these steroids is regulated by a number of enzymes. The enzyme aromatase is the rate limiting enzyme in the non-reversible conversion of the androgen hormones, testosterone and androstenedione, to the estrogen hormones, estradiol and estrone. Compounds such as aromatase inhibitors may thus regulate or inhibit androgen to estrogen conversion, and have therapeutic utility in treating clinical conditions potentiated by the presence of estrogens.

19-Nordeoxycorticosterone (19-norDOC) is known to induce mineralocorticoid hypertension. In the biosynthetic formation of 19-norsteroids, such as 19-norDOC, the initial step is the adrenal hydroxylation of an appropriate steroid such as deoxycorticosterone (DOC). The inhibition of the biosynthetic formation of 19-norDOC by inhibition of 19-hydroxylation of DOC would thus serve to decrease the level of 19-norDOC present in the animal involved and reduce hypertensive effects attributable to the presence of this material.

SUMMARY OF THE INVENTION

The present invention is directed to 2,19-bridged steroidal aromatase and 19-hydroxylase inhibitor compounds, their related intermediates, and the process for their preparation. These compounds may be represented by the following formulas:

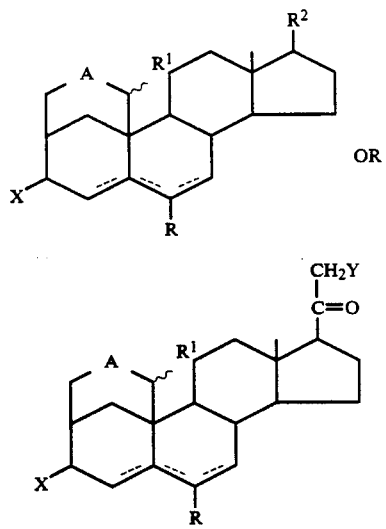

wherein
⸺ represents a single or double bond,
A is O, S, SO, or $SO_2$,
R is H, $=CH_2$, $=O$, or —OH,
$R^1$ is H or $C_{1-4}$ alkyl,
$R^2$ is $\alpha O$, —OH, or —O—($C_{1-4}$ alkanoyl), and
Y is H, —OH, or —O—($C_{1-4}$ alkanoyl), and when Y=H, OH, or —O—($C_{1-4}$ alkanoyl), X may not include —OH, and R may not include =O or —OH.

Examples of the alkyl groups referred to above are methyl, ethyl and propyl. Examples of the alkanoyl groups referred to above are acetyl, propionyl and butyryl. The double bonds, as represented by the dotted lines above are selected in such a way that the compounds must contain at least one double bond, usually in the A-ring of the standard steroid skeleton, although it can also be located at the 5,6-position in the B-ring. If the double bond is located at the 5,6-position, then the other dotted lines represent single bonds. When the system is doubly unsaturated, the double bonds are located at the 4,5- and the 6,7-positions.

Since the compounds of the present invention can be considered as containing a bridged steroid structure, it is possible to name them as derivatives of the basic steroid involved. When this is done with the oxygen-bridged compounds of the present invention, the compounds can be referred to as 2,19-(methyleneoxy) steroids. This indicates that a —$CH_2O$— group connects the 2- and 19-positions with the carbon attached on the 8-side of the 2-position and the oxygen attached to the 19-carbon atom. The sulfur bridged compounds can be described in a similar way.

DETAILED DESCRIPTION OF THE INVENTION

The compounds of the present invention are inhibitors of aromatase and 19-hydroxylase. As aromatase inhibitors, they are useful in treating hyperestrogenemia. The compounds are useful in controlling abnormally high levels of estrogens, both when the high levels observed are relatively steady, or when there are brief surges of elevated levels occurring as part of cyclical body functions. Both females and males can be treated, although obviously, the level of estrogens which would be considered high in males would be much lower than the amount considered high in females. These compounds are also useful as anti-fertility agents to prevent ovulation or implantation in females, or to reduce the mating behavior in males where brain aromatization is required for such behavior. These compounds further have value in treating gynecomastia, male infertility resulting from elevated estrogen levels, and hyperestrogenemia, which may precede myocardial infarction. The compounds also may be used to treat breast cancer and other various estrogen-induced or estrogen-stimulated tumors and hyperplastic tissue disorders.

The bioconversion of deoxycorticosterone via a 19-hydroxylase pathway to 19-nordeoxycorticosterone potentiates its mineralocorticoid activity. Mineralocorticoid excess results in a syndrome characterized by hypokalemia, metabolic alkalosis, polydipsia, polyuria, and hypertensive conditions. Increased excretion of 19-nordeoxycorticosterone has been reported for hypertensive patients, including those with primary aldosteronism, Cushing's syndrome, 17β-hydroxylase deficiency, and individuals with essential hypertension. As 19-hydroxylase inhibitors, these compounds may be useful as antihypertensive agents and for management of edemous conditions often associated with sodium retention and potassium loss.

The compounds of the present invention which have a pregnane side chain are further useful in that a $C_{17-20}$ lyase enzyme can cleave the indicated side chain to give the corresponding 17-oxygenated androstane compounds which, as already indicated, are useful as aromatase inhibitors.

To achieve their desired effect, the compounds of the present invention may be administered orally, parenterally, for example, intravenously, intraperitoneally, intra-muscularly, or subcutaneously, including the injection of the active ingredient directly into tissue or tumor sites, to a patient in need of treatment. The term patient is taken to mean a warm-blooded animal, for example, mammals such as humans, primates, cattle, dogs, cats, horses, sheep, mice, rats, and pigs. These compounds may also be administered in the form of a pharmaceutical preparation, and may further be incorporated into sustained delivery devices. The amount of compound administered will vary over a wide range and be any effective amount. Depending on the patient to be treated, the condition to be treated, and mode of administration, the effective amount of compound administered will vary from about 0.01 to 150 mg/kg of body weight per day, and preferably from about 0.1 to 50 mg/kg body weight per day.

For oral administration, the compounds can be formulated into solid or liquid preparations, such as capsules, pills, tablets, troches, powders, solutions, suspensions, or emulsions. The solid unit dosage forms can be a capsule which can be of the ordinary gelatin type containing the active compound and a carrier, for example, lubricants and inert filler such a lactose, sucrose and corn starch. In another embodiment, an active compound of the invention can be tableted with conventional tablet bases such as lactose, sucrose and corn starch in combination with binders such as acacia, corn starch, or gelatin, disintegrating agents such as potato starch, or alginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose and related sugar solutions, alcohols and glycols, such as propylene glycol or polyethylene glycol are preferred liquid carriers, particularly for injectable solutions.

The compounds can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic ®, silicone rubber manufactured by Dow Corning Corporation. Further information on suitable pharmaceutical carriers and formulation techniques are found in standard texts such as *Remington's Pharmaceutical Sciences*, Mack Publishing Company, Easton, Penna.

Inhibition of aromatase activity is demonstrated by using laboratory methods similar to procedures described in U.S. Pat. No. 4,322,416, and as published in Johnston et al., *Endocrinology* 115:776, 1984, and Burkhart et al., *Steroids* 45:357, 1985.

In this assay, the inhibitor is preincubated with enzyme prior to assaying for activity in the presence of high substrate levels. A time-related decrease in enzyme activity can be indicative of irreversible binding of the inhibitor with the enzyme.

In the time-dependent assay, an amount of the enzyme inhibitor in 100 µl of the assay buffer described above which will provide assay concentrations which are usually between 1 nM and 10 µM are added to 35 ml centrifuge tubes containing 600 µl of the NADPH generating system. The preincubation is started by the addition of 700 µl of aromatase preparation, usually 500–800 µg of microsomal protein per ml of assay buffer. These preparations are mixed using a vortex mixer and incubated for 0, 10, 20, or 40 minutes at 25° C. Then 100 µl of androstenedione ($\sim$6.8 µM) containing 1$\beta$-$^3$H androstenedione is added in assay buffer to provide an assay concentration of substrate (0.55 µM) which is at least ten times the $K_m$ of androstenedione (0.04 µM). Following vortexing, the enzyme incubation is continued for 10 minutes before being terminated by the addition of chloroform. The amount of radioactivity in the aqueous fraction is determined by scintillation procedures. The enzymatic activity for each concentration of inhibitor at each time period of preincubation is calculated as a percent of the "0" minute vehicle control arbitrarily set at 100%. Therefore, the present enzyme inhibition is expressed as a percentage: (100 percent minus percent enzyme activity with inhibitor present).

Enzyme kinetic analysis utilized Kitz-Wilson plots for time-dependent assays. These analyses provide estimates of apparent Ki of inactivation which represents the inhibitor concentration required to produce half-maximal rate of enzyme inactivation. The pseudo first-order rate constant for enzyme inactivation (kcat) and the half-time of inactivation ($\tau_{50}$) of infinite inhibitor concentrations were determined. The ratio of $k_{cat}/K_i$ (inactivation) provides an index number which increases with increased efficiency of enzyme inactivation and increased inhibitor affinity for the enzyme active site. When tested by this procedure, the following results were observed for compounds of this invention:

[3R-(3α,6aα,6bα,8aβ,11aα,11bβ)]-3,4,6b,7,8,8a,10,11,11a, 11b,12,13-dodecahydro-8a-methyl-6H-3,6a-methanocyclopenta[5,6]naphth [1,2-c]oxocin-2,9-dione [Compound (4) below]: $K_i$ (nM)=17.6; $\tau_{50}$ (min)=2.86; $k_{cat}/K_i$=227,300.

[3R-(3α,6aα,6bα,8aβ,11aα,11bβ)}]-3,4,6b,7,8,8a,10,11,11a, 11b,12,13-dodecahydro-8a-methyl-6H-3,6a-methanocyclopenta[5,6]naphtho[1,2-c]thiocin-2,9-dione [Example 3, last paragraph]: $K_i$ (nM)=53.0; $\tau_{50}$ (min)=1.65; $k_{cat}/K_i$=132,103.

[3R-(3α,6aα,6bα,8aβ,11aα,11bβ)]-3,4,6b,7,8,8a,10,11,11a, 11b-decahydro-8a-methyl-6H-3,6a-methanocyclopenta[5,6]-naphth[1,2-c]oxocin-2,9-dione [Compound (15) below]: $K_i$ (nM) =21.6; $\tau_{50}$ (min)=2.82; $k_{cat}/K_i$=189,658.

When assaying compounds for 19-hydroxylase inhibiting activity, compounds were solubilized in dimethyl sulfoxide (DMSO) at 10 mM and diluted in DMSO to provide 0.01–10 µM final concentration when 2 µL aliquots were added to microcentrifuge assay tubes. Assay buffer (10 mM KCl, 1 mM EDTA, 100 mM Tris-HCl at pH 8.0) which had been supplemented with an NADPH-generating system to provide assay concentrations of 1 mM NADPH, 3 mM glucose-6-phosphate and 1 I.U./ml glucose-6-phosphate dehydrogenase were incubated at 37° C. for 5 minutes prior to addition of hamster adrenal mitochondrial protein. Aliquots (180 μL) of this latter preparation containing 5.1 μg enzyme protein were assayed at 37° C. for 5 minutes following the initiation of the assay by the addition of 20 μL of assay buffer containing radio-labelled DOC (0.85 μM final concentration, 0.01 μCi with 99.8% radiochemical purity, NEN Research Products, Boston, Mass.). Assays were quenched by the addition of 800 μL of 20% $CH_3CN$-2% HOAc. The reactants were centrifuged for 2 minutes at 15,000xg and analyzed by liquid chromatography (Beckman Instruments Inc., San Ramon, Calif.) on two $C_{18}$ Radial Pak columns (Waters, Millipore Corporation, Milford, Mass.) in series (5 μM particles, 0.8×10 cm each). Chromatographic buffer A was 10% $CH_3CN$-0.1% HOAc and buffer B was 80% $CH_3CN$-0.1% HOAc. The column was eluted at a flow rate of 1 ml/minute with a linear gradient from 0 to 30% buffer B over 36 minutes followed 100% buffer B. The amount of remaining labeled DOC substrate and initial hydroxylated products, corticosterone and 19-hydroxy-DOC, were separated and the radioactivity contained in each peak quantitated. The 19-hydroxylase activity was based on the quantity of radiolabeled DOC metabolized, since corticosterone and 19-hydroxy-DOC are the products of a single enzyme.

Unlabeled steroids were monitored by their absorbance at 240 nm with a Kratus Spectroflow 773 detector (Kratus Analytical Instruments, Ramsey, N.J.). The extinction coefficients for derivatives of DOC were assumed to be similar to that of DOC ($\epsilon - 17,200$ $M^{-1}cm^1$). Radioactivity of DOC metabolites was measured using an online Flow-One scintillation spectrometer (Radiomatic Instrument & Chemical Co., Inc., Tampa, Fla.) with a 1 ml flow cell.

Time-dependent enzyme inhibition was evaluated by preincubating the enzyme with steroidal compound for either 0 or 60 minutes at 37° C. prior to the addition of radiolabeled substrate for a 5 minute assay. Apparent $K_m$ for the first hydroxylation of DOC may be estimated by the double reciprocal plot of Lineweaver-Burk. $IC_{50}$'s may be graphically estimated from linear-log plots of enzyme activities and log of inhibitor concentrations.

Various procedures can be used to prepare the compounds of the present invention. Scheme 1 below is used to prepare compound (4), [3R-(3α,6aα,6bα,8aβ,-11aα,11bβ)]3,4,6b,7,8,8a,-10, 11,11a,11b,12,13-dodecahydro-8a-methyl-6H-3,6a-methanocy-clopenta[5,6]naphth[1,2-c]oxocin-2,9-dione. Alternatively, compound (4) may be named 2,19-(methyleneoxy) androst-4-ene-3,17-dione. To facilitate the understanding of the present invention, steroidal nomenclature and numbering are utilized in the procedures and examples that follow.

SCHEME 1

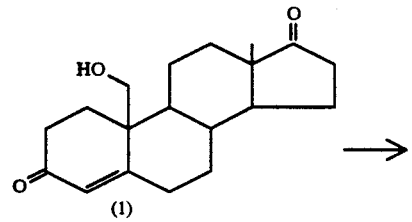

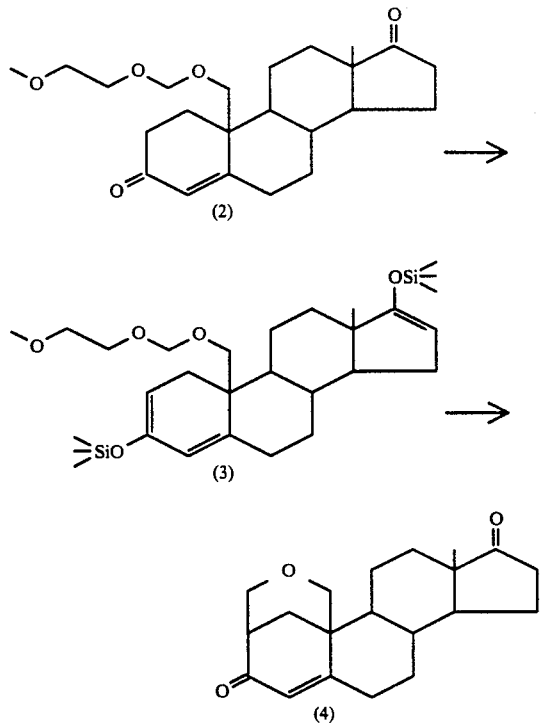

Commercially available steriod starting compound (1) is reacted with diisopropylethylamine and 1-chloro-2,5-dioxahexane to form the compound, 19-[(2-methoxyethoxy)methoxy]-androst-4-ene-3,17-dione (2). This compound is then reacted with a mixture of trimethylchlorosilane and lithium diisopropylamide to form the compound 19-[(2-methoxyethoxyl)methoxy]-3,17-bis[-trimethylsilyl)oxy]-androst-2,4,16-triene (3). This compound is then treated with $TiCl_4$ to give the desired compound, 2,19-(methyleneoxy)androst-4-ene-3,17-dione (4). Alternatively, to prepare those compounds wherein A=S, the corresponding 19-mercapto steroidal starting compound is utilized, and the reaction proceeds analogous to Scheme 1. The compounds where A=SO and A=$SO_2$ are prepared from the corresponding compound where A=S by treatment with one or two equivalents of 3-chloroperoxybenzoic acid, respectively, in a solvent such aas methylene chloride.

To prepare the compound bearing the hydroxyacetyl substituent at the 17-position (10), Scheme 2 is utilized:

SCHEME 2

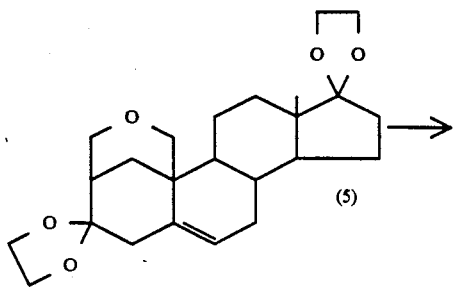

-continued
SCHEME 3

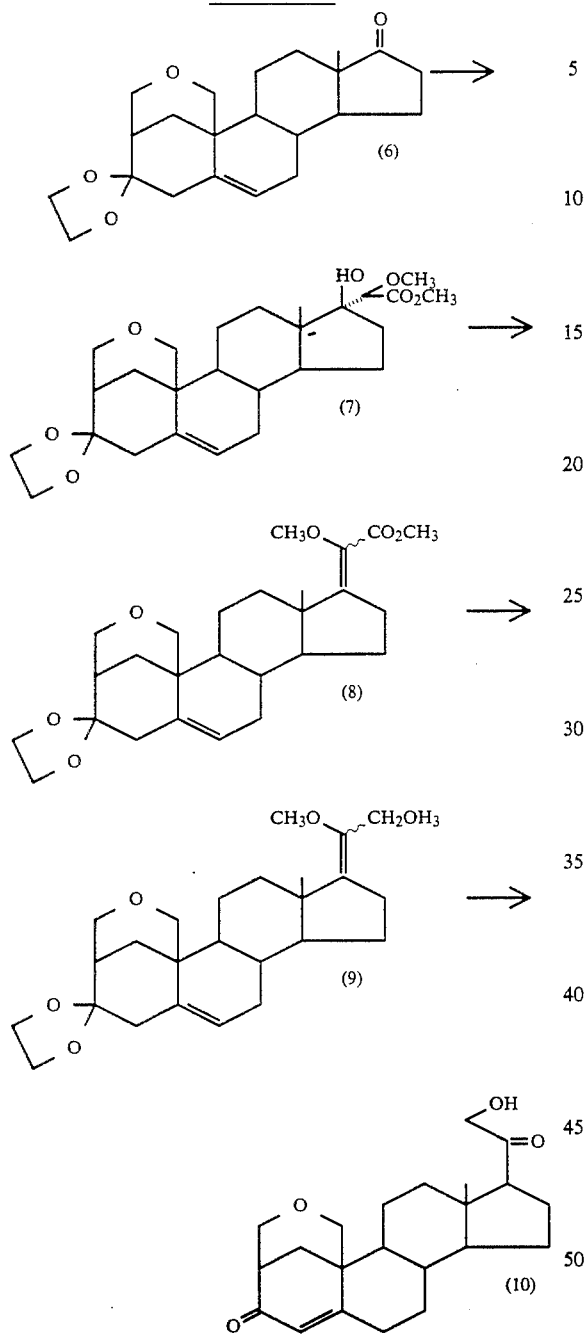

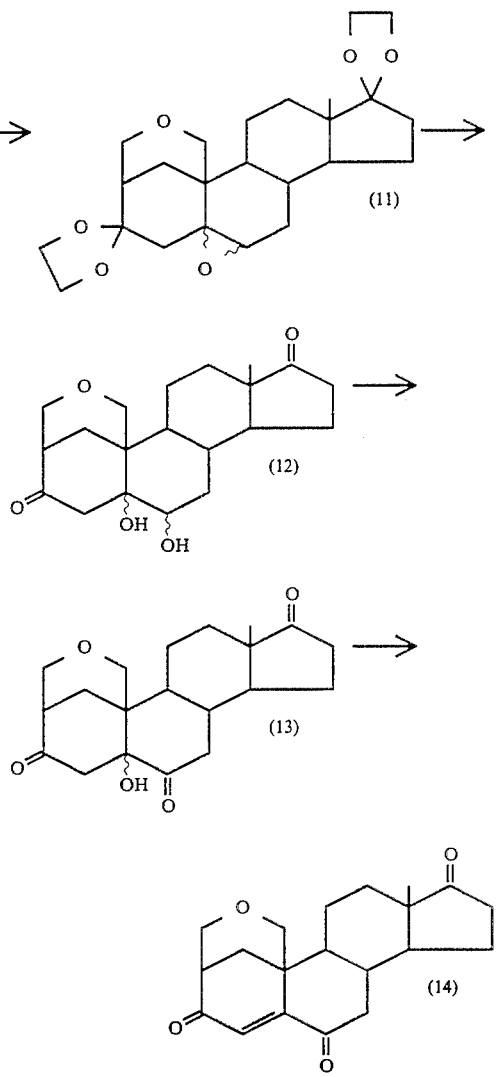

corresponding alcohol (9), which is then further treated with acid to hydrolyze the enol ether and also the 3-ketal to give the desired 21-hydroxy-20-keto compound (10).

To prepare compound (14), 2,19-(methyleneoxy)androst-4-ene-3,6,17-trione, Scheme 3 is utilized:

The 2,19-(methyleneoxy)androst-4-ene-3,17-dione (4) is treated with a catalytic amount of acid such as methane-sulfonic acid in an excess of ethylene glycol to form the corresponding 3,17-bis(ethylenedioxy) compound (5). This compound is then selectively hydrolyzed at the 17-position with 0.15% aqueous perchloric acid in t-butanol and dichloromethane to give the corresponding 17-ketone (6). The ketone is then reacted with methyl methoxyacetate and lithium diisopropylamide wherein upon the indicated ester (i.e., the methylene group thereof), adds across the 17-ketone to give the 17-substituted 17-hydroxy steroid (7). Dehydration introduces a 17-exocyclic double bond and the resulting methoxy ester (8) is reduced with a hydride reducing agent such as diisobutylaluminum hydride to give the The diketal starting materiakl (5) is treated with m-chloroperbenzoic acid in dichloromethane at 0° C. to produce the epoxide (11). The epoxide is opened to the corresponding diol (12) using perchloric acid in THF and H₂O. The ketals are also removed in this process. The diol is then oxidized to the hydroxy-keton by Jones oxidation. The hydroxy-keton (13) is then taken up in benzene and dehydrated using p-toluenesulfonic acid to yield the steroidal trione (14).

Compounds containing multiple double bonds on the steriod ring system can be obtained by dehydrogenation of the appropriate of 2,19-(methyleneoxy)androst-4-ene-3,17-dione (4) with chloranil in t-butanol gives the corresponding diene (15) as shown by Scheme 4 below.

SCHEME 4

(4) →

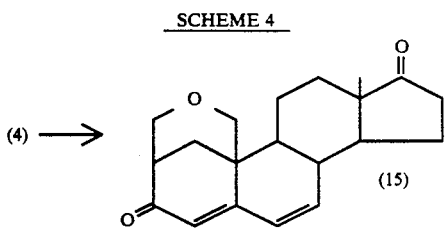

To obtain compounds of the present invention wherein R is =CH$_2$, 2,19-(methyleneoxy)androst-4-ene-3,17-dione (4) is reacted with a formaldehyde acetal as shown by Scheme 5 below.

SCHEME 5

(4) →

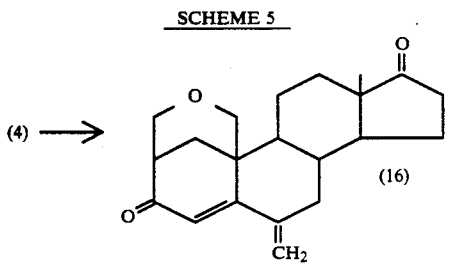

Reagents such as p-toluenesulfonic acid, strong mineral acids, acidic ion exchange resin, or preferably, phosphoryl chloride with formaldehyde dimethyl or diethyl acetal, are most suitable to effect this condensation.

To obtain 2,19-(methyleneoxy)androst-4-ene-3,17-diol (17), Scheme 6 is utilized:

SCHEME 6

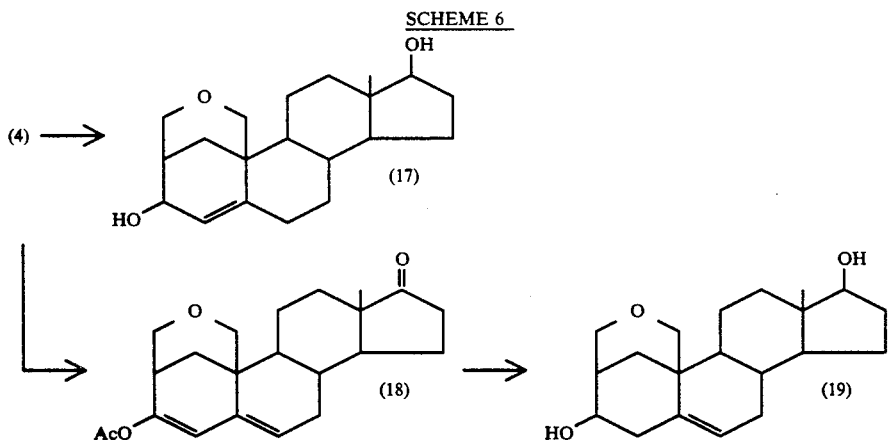

The starting compound, 2,19-(methyleneoxy)androst-4-ene-3,17-dione (4), is reduced with sodium borohydride in ethanol to yield the corresponding diol (17). To prepare the 5,6-ene diol (19), the starting compound, 2,19-(methyleneoxy)androst-4-ene-3,17-dione (4), is treated with a catalytic amount of p-toluenesulfonic acid and heating in a solvent such as Ac$_2$O. The mixture is then cooled. To this mixture is then added pyridine followed by ethanol to yield the dienol acetate (18).

Alternatively, the dienol acetate (18) may preferably be prepared by adding an excess of Ac$_2$O and a catalytic amount of 70% aqueous HClO$_4$ to the steroid (4) in EtOAc. The mixture is then stirred for 15 minutes and poured into dilute Na$_2$CO$_3$, extracted, and washed with dilute Na$_2$CO$_3$ and brine to yield the dienol acetate (18).

The dienol acetate (18) is then treated with calcium borohydride in EtOH at −15° C. The reaction is quenched with HOAc and partitioned between EtOAc and H$_2$O to yield the diol (19). Treatment of the diol (19), with an anhydride, such as acetic anhydride, gives the corresponding diacetate.

In another approach to the preparation of the 5,6-ene diol (19), the steroid (4) is reacted with hexamethyldisilazane in pyridine solution and trimethylbromosilane to give 2,19-(methyleneoxy)-3,17-bis-(trimethylsilyloxy)androsta-3,5,16-triene which is then reduced with calcium borohydride in ethanol to give, after appropriate quenching, the desired product.

To prepare the compound wherein R$^1$ is CH$_3$, Scheme 7 is utilized.

SCHEME 7

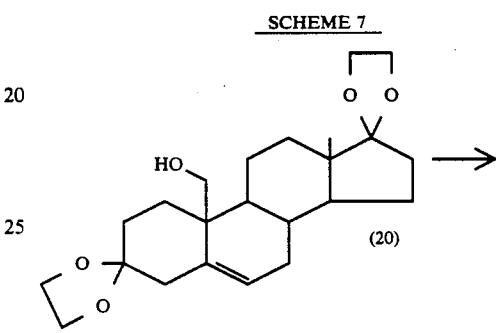

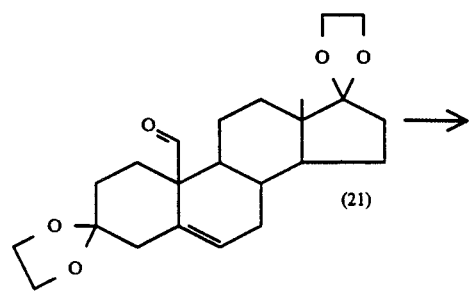

-continued
SCHEME 7

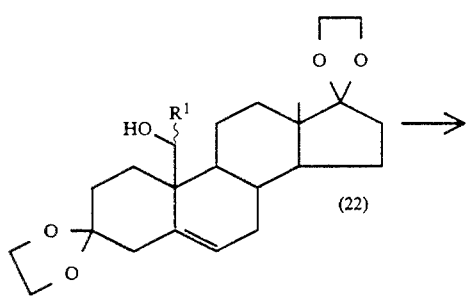

(22)

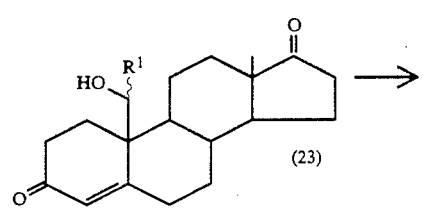

(23)

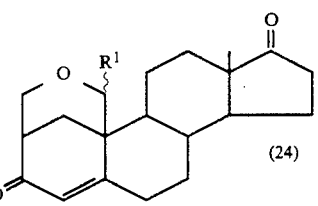

(24)

The known bisketal compound (20) undergoes a Swern oxidation to yield the oxidized bisketal (21). This compound is then treated with R$^1$MgBr or R$^1$Li, wherein R$^1$ is defined above, to produce the R$^1$-substituted hydroxy compound (22). Treatment of 22) with aqueous HCl in the THF yields the dione (23). Treatment of the dione (23) in a manner analogous to Scheme 1 yields the R$^1$-substituted 2,19-(methyleneoxy)-androst-4-ene-3,17-dione (24).

To prepare the compound wherein X is =CH$_2$, Scheme 8 is utilized.

SCHEME 8

(6) →

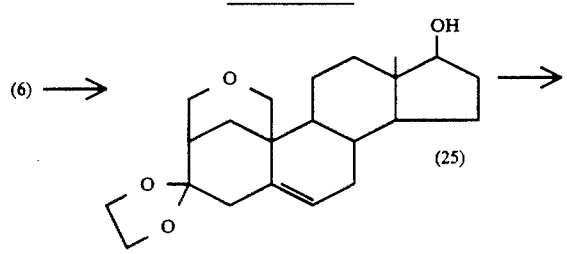

(25)

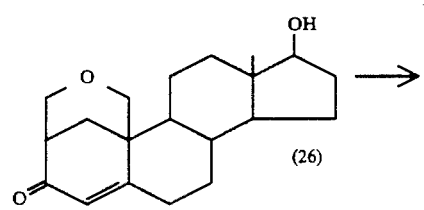

(26)

-continued
SCHEME 8

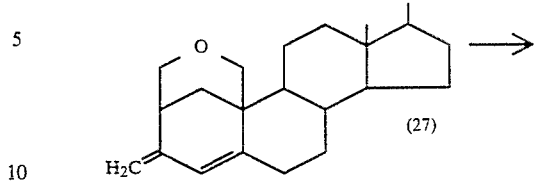

(27)

(28)

To the starting 17-keto compound (6), in EtOH, at 0°60 C., is added an excess of NaBH$_4$. After 30 minutes, the reaction is quenched with CH$_3$COCH$_3$ and concentrated. The residue is added to CH$_2$Cl$_2$, washed with 0.5 N hydrochloric acid solution, water, then brine to yield the corresponding 17-hydroxy compound (25). To this compound 25) in THF is added aqueous hydrochloric acid solution to form the corresponding 3-keto-17-hydroxy compound (26). This compound (26) is then treated with (C$_6$H$_5$)$_3$P=CH$_2$ to yield the corresponding 3-methylene-17-hydroxy compound (27). This compound is then oxidized at C-17 by Jones oxidation to form the 3-methylene-17-keto compound (28). Optionally, compound (28) may then be treated in a manner analogous to Scheme 2 to form the corresponding 21-hydroxy-20-keto compound.

The following examples are provided to illustrate the present invention. They should not be construed as limiting it is any way.

EXAMPLE 1

To a stirred solution of 19-hydroxyandrost-4-ene 3,17-dione (1) (4.54 g, 15.0 mmol) in CH$_2$Cl$_2$ (40 ml) under argon atmosphere was added diisopropylethylamine (5.23 ml, 30.0 mmol) followed by 1-chloro-2,5-dioxahexane (2.57 ml, 22.5 mmol). After 20 hours, the reaction was diluted with CH$_2$Cl$_2$ (60 ml) and the organics were washed with H$_2$O (75 ml), 0.5 N hydrochloric acid (2×75 ml), saturated NaHCO$_3$ (35 ml), and brine (75 ml). Drying (MgSO$_4$) and concentration gave an orange oil (6.33 g). The oil was dissolved in 10 ml of EtOAc/hexane (65:35) and loaded onto a column. Flash chromatography (7.5×15 cm silica gel column), eluting with EtOAc/hexane (65:35) gave 19-[(2-methoxyethoxy)methoxy]-androst-4-ene-3,17-dione (2). (Weight: 4.44 g). HRMS calculated for C$_{23}$H$_{34}$O$_5$ (M+): 390.2406; found M+: 390.2401; error=−1.3 ppm.

EXAMPLE 2

To a stirred solution of diisopropylamine (0.37 ml, 2.65 mmol) in THF (7 ml) under argon and cooled to −20° C. was added n-BuLi (1.03 ml, 2.42 M in hexane, 2.49 mmol). After 12 minutes, a cooled (−20° C.) solution of trimethylchlorosilane (0.74 ml, 5.81 mmol) in THF (1 ml) was added rapidly. After 2 minutes, a cooled (−20° C.) solution of the product of Example 1 (2) (324 mg, 0.83 mmol) in THF (2 ml) was added dropwise followed by a 0.5 ml THF rinse. The reaction was stirred at −20° C. for 30 minutes and then allowed to warm slowly to room temperature. The reaction was stirred at room temperature for 30 minutes, triethylamine (1 ml) was added and the reaction was diluted to a 50 ml volume with ethyl ether. The organics were washed with saturated NaHCO$_3$ (50 ml+20 ml) followed by brine/saturated NaHCO$_3$ (20 ml of a 3:1 mixture). Drying (MgSO$_4$) and concentration gave a pale yellow oil. To this product was added hexane, the mixture concentrated, and then placed under high vacuum for 5 minutes to remove any remaining THF and triethylamine, yielding 19-[(2-methoxyethoxy)methoxy]-3,17-bis-[(trimethylsilyl)oxy]androsta-2,4,16-triene (3) (quantitative).

EXAMPLE 3

To a stirred solution of the product of Example 2 (3) (0.83 mmol) in CH$_2$Cl$_2$ (8 ml) under argon and cooled to -20° C was rapidly added a TiCl$_4$ solution (2.49 ml of a 1M TiCl$_4$ in CH$_2$Cl$_2$ solution, 2.49 mmol). A tan suspension resulted. Additional CH$_2$Cl$_2$ (8 ml) was added. The reaction suspension was stirred at −20° C. for 35 minutes, diluted with CH$_2$Cl$_2$ and poured into saturated NaHCO$_3$. The layers were separated and the aqueous layer was extracted with additional CH$_2$Cl$_2$. The combined organics were washed with saturated NaHCO$_3$ (2x), 0.5N hydrochloric acid (1x), followed by brine. Drying (MgSO$_4$) and concentration gave a milky oil. To this product was added 4 ml of EtOAc/hexane (50:50), the solid was crushed, and the suspension was heated with a heat gun and then allowed to cool to room temperature prior to loading the supernatant onto a flash column for chromatography (2×10 cm silica gel column). The supernatant was loaded as stated, eluted with EtOAc/hexane (50:50), and 15-20 ml fractions were collected. Concentration of the product containing fractions gave a pale yellow oil. Et$_2$O was added to the residue and the flask was swirled to provide a solid. Concentration gave an oily, white solid (0.14 g). This product was then triturated with 2 ml of Et$_2$O/hexane (3:1). As much solid as possible was scraped from the side of the flask and the suspension was filtered to provide a white solid (56 mg). The solid was dried under high vacuum over refluxing acetone for 6 hours, yielding the compound of the formula below, mp 204°-213° C. [3R-(3α,6aα,6bα,8aβ,11aα,11bα-8)-3,4,6b,7,8,8a,10,11,11a,11b,12,13-dodecahydro-8a-methyl-6H-3,6a-methanocyclopenta[5,6]naphth[1,2-c]oxocin-2,9-dione, or alternatively named, 2,19-(methyleneoxy)androst-4-ene-3,17-dione. (Weight remained 56 mg.).

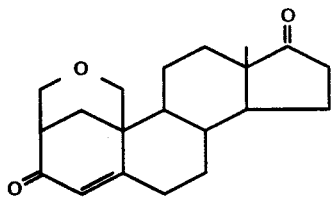

Elemental analysis: Calculated for C$_{20}$H$_{26}$O$_3$: C, 76.40; H, 8.34. Actual: C, 76.60; H, 8.53.

The corresponding sulfur compound, 2,19-(methylenethio) androst-4-ene-3,17-dione, was obtained in an analogous manner and melted at 183°-199° C. This compound can also be [3R-(3α,6aα,6bα,8aβ,11aα,11bβ)]-3,4,6b,7,8,8a,10,11, 11a,11b,12,13-dodecahydro-8a-methyl-6H-3,6a-methanocyclopenta[5,6]naphtho[1,2-c]thiocin-2,9-dione.

EXAMPLE 4

The product of Example 3 was treated with a catalytic amount of methanesulfonic acid and an excess of ethylene glycol in solvent (benzene) and heated to reflux under DeanStark conditions to form the corresponding 3,17-bis(ethylenedioxy)-5-ene compound (5).

EXAMPLE 5

A solution of the product of Example 4 in dichloromethane and t-butanol was treated with 0.15% aqueous perchloric acid. The mixture was heated at gentle reflux for two hours with stirring and then allowed to cool to room temperature. The reaction mixture was then poured into saturated sodium carbonate solution and extracted into EtOAc. The EtOAc extract was washed with water and brine, dried over magnesium sulfate, concentrated, and chromatographed on silica gel eluting with EtOAc/hexane (2:3) to give the corresponding 17-one compound (6).

EXAMPLE 6

A solution of methyl methoxyacetate in tetrahydrofuran was slowly added to a cold solution of lithium diisopropylamide, prepared from diisopropylamine and n-butyl lithium in hexane, in the same solvent. A solution of the product of Example 5 in tetrahydrofuran was then added dropwise over 5-10 minutes and the solution is stirred for three hours at the same temperature. Saturated aqueous ammonium chloride solution was then added dropwise, and the mixture was poured into ice water and extracted with ethyl acetate. The extract was washed with brine, dried over sodium sulfate, filtered, and concentrated to afford the 17-substituted steroid (7). The crude product was chromatographed on silica gel, eluting with 1:1 ethyl acetate:hexane to afford the product as a mixture of isomers.

EXAMPLE 7

A solution of the product of Example 6 in pyridine and CH$_2$Cl$_2$ was chilled to 0° C. and treated dropwise with thionyl chloride over 5-10 minutes. After stirring for 75 minutes at the same temperature, the solution was poured into ice water. The organic layer was washed twice with brine, dried over sodium sulfate, filtered and concentrated to afford crude product. Flash chromatography (30% ethyl acetate/70% hexane) afforded the methoxyester (8).

EXAMPLE 8

A solution of the product of Example 7 in toluene was chilled to −20° C. and treated dropwise with a 20% solution of diisobutylaluminum hydride in hexane. The solution was stirred at −20° C. for 30 minutes. Water was added and the mixture was stirred at 0° C. for 20 minutes, poured into ice water and extracted with 3:1 ether:dichloromethane. The extracts were washed with brine, dried over sodium sulfate, and concentrated. The residue was subjected to flash chromatography eluting with 3:2 ethyl acetate:hexane to afford the alcohol (9).

EXAMPLE 9

To a solution of the product of Example 8 in THF was added 0.5 N aqueous HCl. After 4 days, the reaction was diluted with CH$_2$Cl$_2$/H$_2$O, the layers separated, and the organics washed with brine, dried over sodium sulfate, and concentrated. The hydroxyketone of the formula below was isolated by flash chromatography (silica gel) eluting with EtOAc/hexane (4:1). HRMS: Calcd for $C_{22}H_{31}O_4$: MH+ 359.2222; Found: MH+ 359.2204; Error: −5.0 ppm.

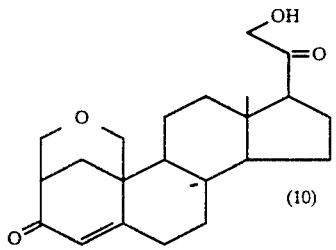

(10)

EXAMPLE 10

To a solution of the product of Example 4 (5) is added m-chloroperbenzoic acid in methylene chloride at 0° C. The mixture is maintained at 0° C. for 16 hours then diluted with methylene chloride and washed with water, 10% sodium carbonate, and brine, then dried and evaporated. Chromatography gives the epoxide (11).

EXAMPLE 11

To a solution of the product of Example 10 (11) in THF and water is added dropwise 70% aqueous perchloric acid and the reaction is stirred at room temperature for 48 hours. The mixture is diluted with methylene chloride, washed with aqueous $Na_2CO_3$ and brine, then dried ($MgSO_4$) and concentrated. Chromatography gives the corresponding diol (12).

EXAMPLE 12

To the product of Example 11 (12) in acetone at 0° C. is added dropwise Jones' reagent until a brown color persists for 15 minutes. The reaction is quenched with methanol. The mixture is then partitioned between methylene chloride and water. The organic phase is washed with brine, and then dired and concentrated. Chromatography gives the hydroxyketone (13).

EXAMPLE 13

To the product of Example 12 (13) dissolved in benzene is added a catalytic amount of p-toluenesulfonic acid. The mixture is heated at reflux for 30 minutes using a Dean-Stark water trap. The cooled solution is then poured into water. The organics are washed with aqueous $Na_2CO_3$ and brine, then dried and evaporated. The residue is chromatographed to afford the trione compound of the formula below, 2,19-(methyleneoxy)androst-4-ene-3,6,17-trione (14).

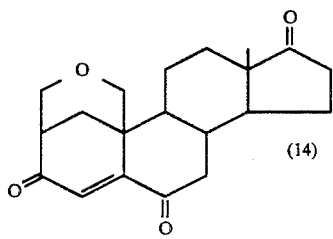

(14)

EXAMPLE 14

To the product of Example 3 (4) in t-butyl alcohol was added chloranil (2.25 equivalents). The mixture was refluxed for 3.5 hours, cooled and filtered and the filtrate concentrated. The residue was taken up in ethyl acetate and washed with water, aqueous NaOH, and brine. Drying and concentration, followed by chromatography afforded the compound [3R-(3α, 6aα, 6bα,-8aβ, 11aα,11bβ)]-3,4,6b,7,8,8a, 10,11,11a, 11b-decahydro-8a-methyl-6H-3,6a-methanocyclopenta[5,6]naphth-[1,2-c]oxocin-2,9-dione of the formula:

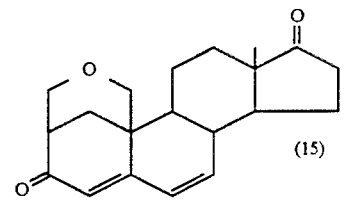

(15)

mp=193°-197° C.

$^1$H NMR (CDCl$_3$): δ 6.32 (dd, 1H, vinyl), 6.22 (dd, 1H, vinyl), 6.04 (s, 1H, vinyl), 3.98 (ddd, 1H, ¼ CH$_2$OCH$_2$), 3.73 (dd, 1H, ¼ CH$_2$OCH$_2$), 3.64 (d, 1H, ¼CH$_2$OCH$_2$), 3.55 (dd, 1H, ¼ CH$_2$OCH$_2$), 0.94 (s, 3H, 18-CH$_3$).

$^{13}$C NMR(CDCl$_3$): δ 219.0, 201.2, 157.8, 138.2, 128.5, 127.9, 69.7, 67.1, 49.1, 48.2, 47.8, 44.2, 38.1, 36.1, 35.5, 31.4, 21.3, 20.5, 13.6.

IR(KBr): 2956, 2854, 1740, 1662 1616 cm$^{-1}$.

EXAMPLE 15

A suspension of sodium acetate in absolute chloroform containing formaldehyde dimethyl acetal and phosphoryl chloride is stirred at reflux for 1 hour. After addition of the product of Example 3 (4), the mixture is treated dropwise with phosphoryl chloride over a period of 2.5 hours. The reaction is subsequently stirred at reflux for the appropriate time. The suspension is allowed to cool and under vigorous stirring a saturated aqueous solution of sodium carbonate is added dropwise until the pH of the aqueous layer becomes alkaline. The organic layer is separated, washed with water, and dried with sodium sulfate. After concentration and purification, the product obtained is the compound of the formula:

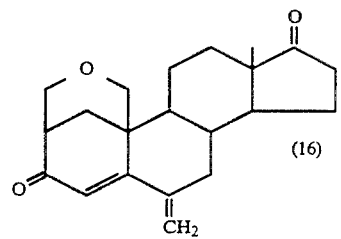

(16)

What is claimed is:
1. A compound of the formula

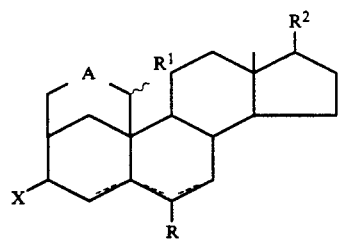

wherein

▭▭ represents a single or double bond, provided there is at least one double bond, A is O, S, SO, or $SO_2$;

R is H, $\alpha CH_2$, =O, or —OH;

$R^1$ is H or $C_{1-4}$ alkyl;

$R^2$ is =O, —OH, —O—($C_{1-4}$ alkanoyl); and

X is =O, =$CH_2$, —OH, or —O—($C_{1-4}$ alkanoyl).

2. A compound according to claim 1 which has the formula

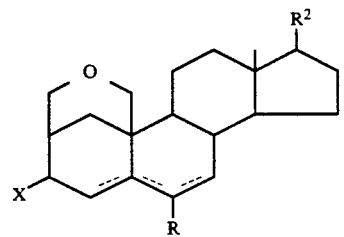

wherein

▭▭ represents a single or double bond, provided there is at least one double bond, and X, R, and $R^2$ defined in claim 1.

3. A compound according to claim 1 which has the formula

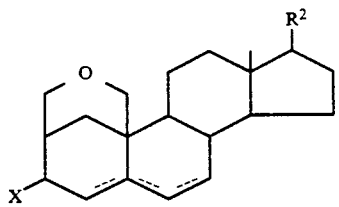

wherein

▭▭ represents a single or double bond, provided there is at least one double bond, and X and $R^2$ are defined in claim 2.

4. A compound of claim 1 which has the formula

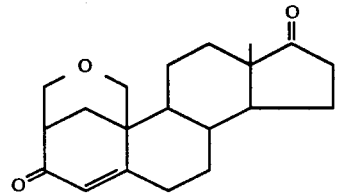

and is [3R-(3α,6aα, 6aα, 6bα, 8aβ, 11aα, 11bβ)]-3,4,6b,7,8, 8a, 10,11,11a,11b,12,13-dodecahydro-8a-methyl-6H-3,6a, methanocyclopenta[5,6]naphth[1,2-c]oxocin-2,9-dione.

5. A compound of claim 1 which is [3R-(3α,6aα,6bα,-8aβ,-11aα,11bβ)]-3,4,6b,7,8,8a, 10,11,11a,11b,12,13-dodecahydro-8a-methyl-6H-3,6a-[5,6]naphtho[1,2-c]thiocin-2,9-dione.

6. A compound of claim 1 which is [3R-(3α,6aα,-6aα,6bα, 8aβ,11aα,11bβ)]3,4,6b,7,8,8a,10,11,11a,11b,-decahydro-8-methyl-6H-3,6a-methanocyclopenta [5,6]naphth[1,2-c]oxocin-2,9-dione.

* * * * *

UNITED STATES PATENT AND TRADEMARK OFFICE
CERTIFICATE OF CORRECTION

PATENT NO. : 5,099,037

DATED : March 24, 1992

INVENTOR(S) : Norton P. Peet, J. O'Neal Johnston and Joseph P. Burkhart

It is certified that error appears in the above-identified patent and that said Letters Patent is hereby corrected as shown below:

```
    Column 1, line 68, "R2 is αO," should read -- R2 is =O, --.
    Column 1, after line 68, make insert to read -- X is =O, =CH2, -OH, or -
O-(C1-4 alkanoyl, and --.
    Column 2, line 24, "8-side" should read -- β-side --.
    Column 4, line 50, "β)}]-" should read -- β)]- --.
    Column 7, line 34 in the formula, "CH2OH3" should read -- CH2OH --.
    Column 7, line 63, "wherein upon" should read -- whereupon --.
    Column 8, line 57, "keton" should read -- ketone --.
    Column 8, line 58, "keton" should read -- ketone --.
    Column 8, line 65, "appropriate of 2,19-" should read -- appropriate
starting compound.  For example, dehydrogenation of 2,19- --.
    Column 11, line 39, "of 22)" should read -- of (22) --.
    Column 12, line 21, "0°60C.," should read -- 0°C, --.
    Column 12, line 26, "25)" should read -- (25) --.
    Column 12, line 43, "CH2C12" should read -- CH2Cl2 --.
    Column 13, line 46, "11bα-8" should read -- 11bβ)] --.
    Column 17, line 17, "αCH2" should read -- =CH2 --.
    Column 17, line 39, "R2 defined" should read -- R2 are defined --.
    Column 18, line 28, "6aα, 6aα, 6bα," should read -- 6aα,6bα, --.
    Column 18, line 34, "3,6a-[5,6]" should read -- 3,6a-
methanocyclopenta[5,6] --.
    Column 18, line 36, "6aα,6aα,6bα," should read -- 6aα,6bα, --.
```

UNITED STATES PATENT AND TRADEMARK OFFICE
CERTIFICATE OF CORRECTION

PATENT NO. : 5,099,037

DATED : March 24, 1992

INVENTOR(S) : Norton P. Peet, J.O'Neal Johnston and Joseph P. Burkhart

It is certified that error appears in the above-indentified patent and that said Letters Patent is hereby corrected as shown below:

In the Abstract, "2,19-methylenoxy" should read --2,19-methleneoxy--.

Signed and Sealed this

Twenty-first Day of September, 1993

*Attest:*

BRUCE LEHMAN

*Attesting Officer*         *Commissioner of Patents and Trademarks*